United States Patent [19]

Wicks

[11] 4,209,015
[45] Jun. 24, 1980

[54] PARENTERAL ADMINISTRATION APPARATUS

[76] Inventor: Anthony E. Wicks, 3 Greenvale Pl., Scarsdale, N.Y. 10583

[21] Appl. No.: 909,119

[22] Filed: May 24, 1978

[51] Int. Cl.² .............................................. A61M 5/00
[52] U.S. Cl. ......................... 128/214.4; 128/DIG. 26
[58] Field of Search ............. 128/214 R, 214.2, 214.4, 128/348, DIG. 26; 27/24 A

[56] References Cited

U.S. PATENT DOCUMENTS

| | | | |
|---|---|---|---|
| 2,528,095 | 10/1950 | Ward | 128/DIG. 26 |
| 2,729,876 | 1/1956 | Hagemann | 128/214 R X |
| 3,537,451 | 11/1970 | Beck | 128/214.4 |
| 3,713,442 | 1/1972 | Walter | 128/214.4 |
| 4,020,835 | 5/1977 | Nordstrom et al. | 128/214.4 |

Primary Examiner—Dalton L. Truluck
Attorney, Agent, or Firm—Martin J. Spellman, Jr.

[57] ABSTRACT

A Parenteral administration apparatus comprising a hollow needle having a sharpened distal end and a proximal end. The proximal end is secured in a tubular base, the interior of the needle being in flow communication with the hollow interior of said tubular base. A relatively flexible elongated tube concentric with said needle and slightly shorter than said needle, and having a distal end in slidingly frictional engagement with the outer surface of said needle is provided. The proximal end of said tube is secured to one end of a hollow cylindrical base which has an annular necked-in portion defined by spaced apart annular shoulders. A spring biased removable handle member comprised of a pair opposed inwardly curved arms biased toward each other and secured against relative longitudinal movement by said shoulders has outwardly extending handle members connected to said arms for causing said curved arms to move open, away from each other and spring means connecting said handle members together to normally urge said arms toward each other.

1 Claim, 3 Drawing Figures

PARENTERAL ADMINISTRATION APPARATUS

BACKGROUND OF THE INVENTION

This invention relates to improved apparatus for the administration of parenteral injections and specifically with apparatus wherein a hollow sharp pointed needle is used to penetrate the flesh and the vein or artery of the patient. Once the lumen of the vein or artery is located with the needle a flexible tube with the distal end in sliding engagement with the needle is advanced over the distal point of the needle which in turn is withdrawn through the central passage of the flexible tube which tube usually extends an inch or two beyond the skin surface and is taped in place flat on the skin when the needle is withdrawn. Then a supply tubing of fluid is attached at the end of the base fixture at the distal end of the tube.

The procedure involved in locating the vein or artery and placing the needle in the lumen of the vein or artery, advancing the flexible tube conduit over the needle into the lumen and withdrawing the needle is often complicated by difficulty in finding the proper vein or artery or one large enough. The failure to make the proper penetration or initial penetration often requires throwing away of the apparatus and starting again. The one administering the treatment often encounters difficulty both in holding the apparatus in place and moving the needle relative to the outer tube or vice-versa because of the lack of a suitable grasp of the tube portion.

It is impractical to form the tube carrier fixture with a handle fixed thereon because once the needle is withdrawn the fixture is usually taped flat along the skin surface of the patient during the administration of the fluid. Thus, the person attempting to administer to the patient often finds himself wishing he had a third or fourth hand to manipulate the apparatus parts relative to each other and to hold the apparatus in place in relation to the desired location on the patient's skin and in relation to the target vein or artery. Due to the nature of the procedure, any device or attachment to facilitate the relative axial movement between the needle and the outer tube must firmly grip one or the other and allow for positive control, yet be removable or inconspicuous after insertion of the catheterization tube in order to allow taping of the tube to the skin surface of the patient with minimum interference and discomfort.

SUMMARY OF THE INVENTION

The present invention is a greatly improved injection device which comprises the hollow needle having the bias distal chisel end thereof sharpened for initial penetration of skin and vein or artery. The proximal end of the needle is secured in flow communication to a from the necked-in portion of the base of the catheter tube.

BRIEF DESCRIPTION OF THE DRAWINGS

In the accompanying drawing.

DESCRIPTION OF PREFERRED EMBODIMENTS

Figure 1:
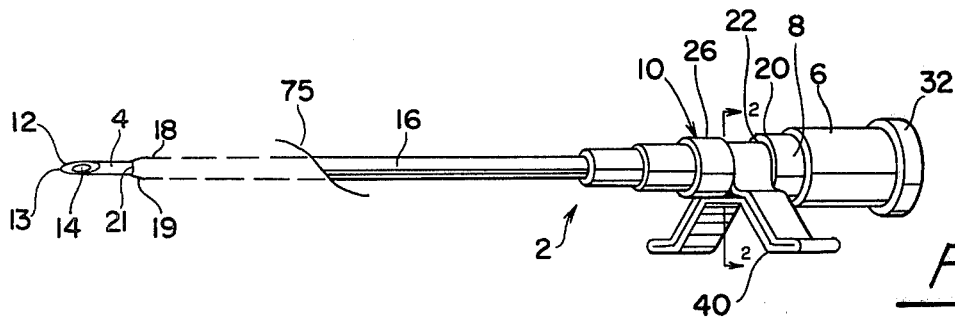
FIG. 1 shows an overall view of the improved injection apparatus going to this invention.

Referring in greater detail to the accompanying drawing, the improved injection apparatus of this invention is indicated in FIG. 1 generally by reference numeral 2 and is comprised of a stainless steel hollow needle 4 carried on a hollow cylindrical base, 6 having a proximal end portion 8 in which the steel needle 4 is retained, and which is normally carried within an outer cylindrical tube casing 10. The needle 4 has a proximal end 12 which has a sharpened bias chisel point 13, the hollow interior axial passage indicated at 14. The needle 4 extends through the hollow cylindrical interior of the flexible plastic tube conduit 16. The proximal end of 18 of the tube 16 is formed with a taper 19 to the outer surface of the needle 4 and the outer surface of the needle 4 is in close sliding engagement therewith. The tapered end 18 facilitates sliding through flesh into the lumen of vein or artery and is tapered 19 down to a relatively sharp cylindrical edge 21. The outer casing 16 has an end portion 20, the outer surface of which is formed with the transverse shoulder 22 which together with oppositely disposed shoulder 26 define the middle necked-in cylindrical portion 24 better shown in sectional FIGS. 2 and 3. The base 20 is provided with successfully reduced cylindrical portions 28 and 30.

Figure 3:
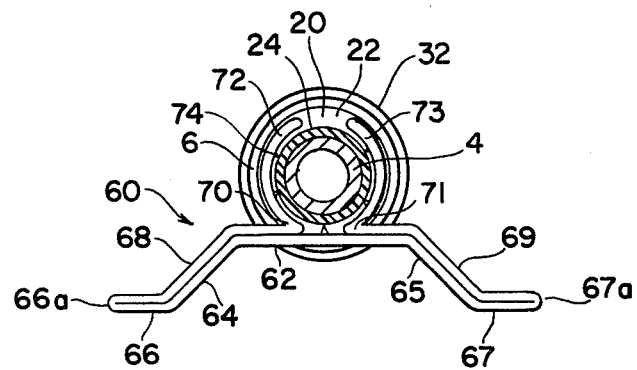
FIG. 3 is an alternate embodiment of the clip similar to FIG. 2.
Figure 2:
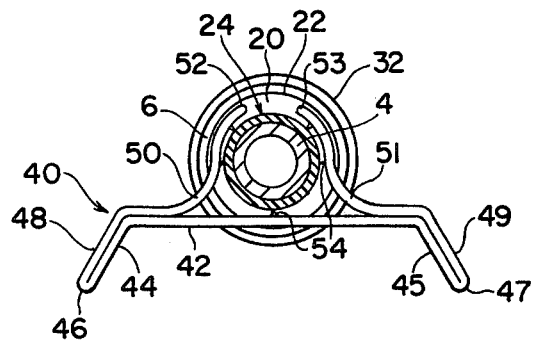
FIG. 2 is a cross-section taken along line 22 FIG. 1.

Referring more particularly to FIGS. 2 and 3, the apparatus 2 includes the clamp 40 which comprises a horizontal transverse portion 42 each end of which is provided with a downwardly and outwardly extending arm 44 and 45 respectively, which extend to, in the embodiment shown, bent over end portions 46 and 47, and these to outer surfaces 48 and 49 forming a pair of wing-like handles respectively. From the wing-like handles there are connected upwardly curved portions 50 and 51 respectively which extend towards the necked-in portion 24 and have inward curves 52 and 53 with radii generally corresponding to that of the necked-in portion 24. The inner portions of the curves 52 and 53 as well as the central portion of the horizontal arm 42 are provided with tooth-like projections 54 to engage the necked-in portion 24 in order to further secure it against unwanted transverse of lateral movement.

FIG. 3 shows a slightly different embodiment of the present invention in which the horizontal arm is indicated at 62 with extending arms 64, 65, with horizontal portions 66 and 67 extending to ends 68a and 67a around to portions 68, 69 and acute curved sections 70 and 71 from which extend curved arms 72 and 73 that are provided within extending projections 74.

The device of the present invention is initially utilized in the same manner as known devices, the point 12 of the needle 4 penetrating the hollow cylindrical base which is adapted for attachment to a flexible fluid supply tubing. The needle is normally removably carried within a flexible catheterization tube which slides in friction engagement over the outer circumferential surface of the needle and is carried by a hollow cylindrical base the end of which is remote from the tube and receives the inner base of the needle, and when the needle is withdrawn, flexible tubing from the fluid supply.

In the device of this present invention the outer surface of cylindrical base of the catheter tube is provided with a necked-in portion defined by two opposed facing shoulder-like surfaces.

A spring biased handle device having two oppositely disposed arms generally curved inwardly with a radii matching that of outer surface curvature of the necked in portion of the base and with interior facing teeth for gripping the necked-in portion and wing-like projections serving as dual handles for the user. The width of the handle device corresponds to the distance between the spaced apart shoulders of the necked-in portion to provide a firm, secure engagement with them. The handle device, provides a suitable means for grasping the injection apparatus to allow facile relative movement between the needle and the catheter tube portion, but once the catheter is inserted may be removed readily in order to secure the apparatus in place on the external skin of the patient. This is accomplished simply by squeezing the wing-like handles toward one another with ones finger to move apart the curved portions and allow the removal of the device skin 75 and subsequently the lumen of the vein or artery. The needle 4 is then withdrawn within the sheath a tube 16 and removed from the outer casing 10 as the conduit tube 16 is held in place within the vein.

The utilization of the clamp member 40 is a great assistance in holding the needle 4 and the outer casing 10 in proper position and manipulating one in axial movement in relation to the other and to the target vein or artery. The cooperation of the curves 52 and 53 with the shoulders 22 and 26 together with the gripping teeth 54 on the necked-in portion 24 provide positive control when it is desired to remove the member 40, finger pressure on the wing surfaces 48 and 49 is sufficient to overcome the biasing and spread the arms 52 and 53 sufficiently to remove the member 40 from the outer casing 10 to permit the casing 10 and tube 8 to be taped to the patient's skin.

The modification shown in FIG. 3 is operated in a similar manner.

It is understood that the above-described arrangements are merely illustrative examples of the application. Numerous other arrangements may be readily devised by those skilled in the art which will embody the principles of the invention and fall within the spirit and scope thereof.

What is claimed is:

1. A parenteral administration apparatus comprising a hollow needle having a sharpened distal end and a proximal end, said proximal end being secured in a tubular base, the interior of the needle being in flow communication with a hollow interior of said tubular base, a relatively flexible elongated tube concentric with said needle and slightly shorter than said needle and having a distal end in slidingly frictional engagement with the outer surface of said needle, the proximal end of said tube being secured to one end of a hollow cylindrical base which base has an annular necked-in portion defined by spaced apart annular shoulders, a spring biased removable handle member comprised of a pair of opposed inwardly curved arms biased toward each other and secured against relative longitudinal movement by said shoulders, said removable handle having outwardly extending handle members connected to said arms for causing said curving arms to move open away from each other, and spring means connecting said outwardly extending handle members together to normally urge said arms toward each other.

* * * * *